April 18, 1972 P. ECKE Plant Pat. 3,120
POINSETTIA PLANT
Filed March 11, 1970
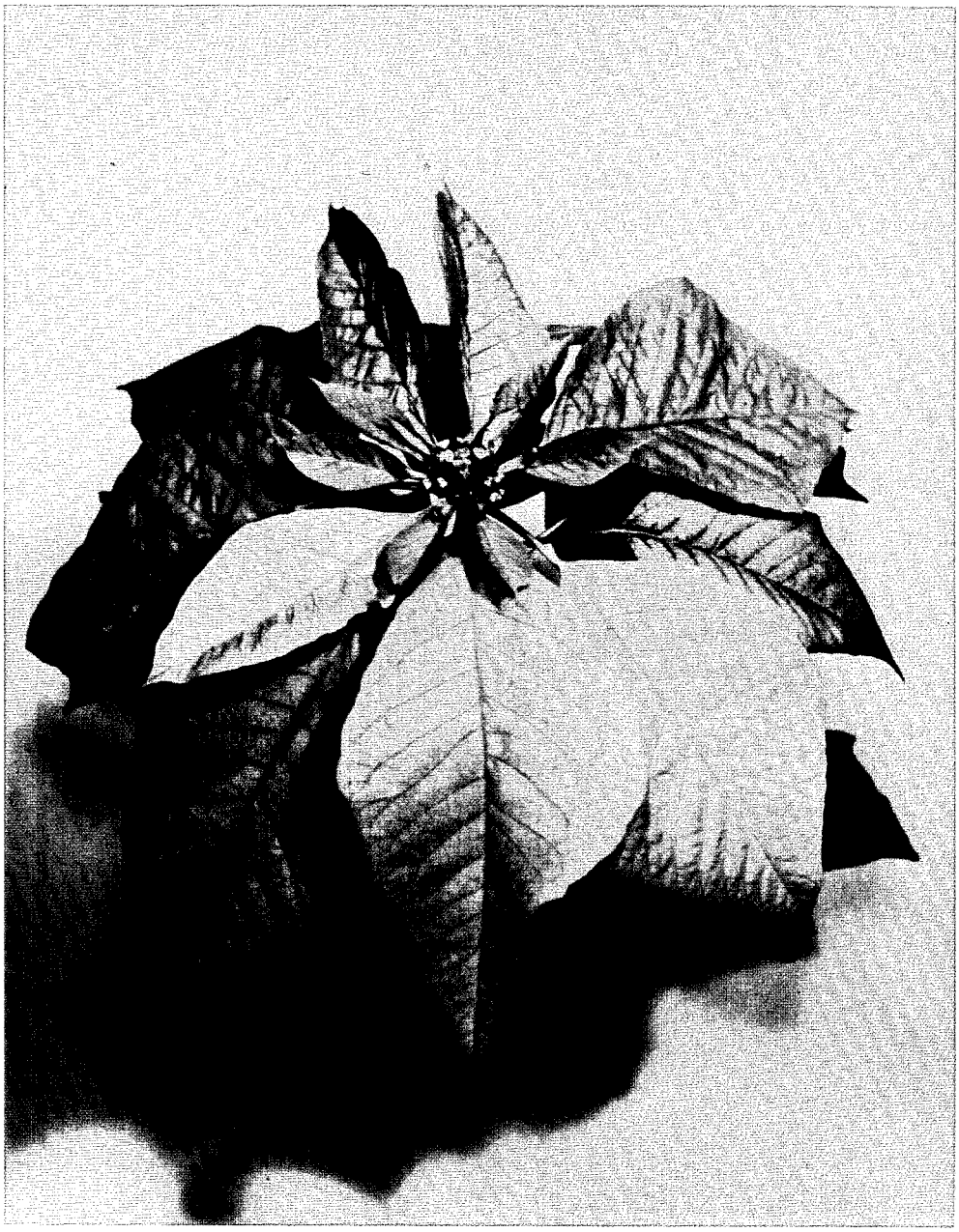
Inventor.
Paul Ecke
By: Robb & Robb
Attorneys.

United States Patent Office

Plant Pat. 3,120
Patented Apr. 18, 1972

3,120
POINSETTIA PLANT

Paul Ecke, Encinitas, Calif., assignor to Paul Ecke, Inc., Encinitas, Calif.

Filed Mar. 11, 1970, Ser. No. 18,772
Int. Cl. A01h 5/00
U.S. Cl. Plt.—86 1 Claim The present invention relates to a new and distinct variety of poinsettia plant (botanically known as *Euphorbia pulcherrima*), which was discovered by me as a cultivated sport of the poinsettia variety known as #C–1 (Plant Patent No. 2,923), said discovery having been made by me in one of the greenhouses maintained by my assignee at Encinitas, Calif.

At the time of my discovery, various poinsettia varieties, including many plants of the patented variety identified as #C–1, were being grown under my personal supervision and care. In the course of these growing operations, my attention was attracted to one particular plant among those of #C–1 which bore bracts of a distinctive and attractive pink color instead of the normal red bracts of #C–1. Close inspection of this particular plant showed that it had sported, and I accordingly took steps to carefully preserve the sport and keep it under close observation. In due course, I asexually reproduced the sport by vegetative cuttings taken therefrom and planted by me in the same greenhouses at Encinitas, Calif. Continued observations and tests of the original sport and its progeny derived therefrom as aforesaid and which have been successfully propagated through many generations, fully confirmed that the pink bracts come true and remain stable. Except for the different bract color, the new sport is substantially identical in all other respects to the variety #C–1, thereby resulting in a new and distinct variety having the following unique and commercially valuable combination of characteristics which are outstanding therein and which distinguish the new sport from all other poinsettia varieties of which I am aware:

(1) A very vigorous, tough and durable plant habit of medium height and having the ability to grow well as a multiple stem and multiple bloom plant;
(2) A very vigorous and extensive root system;
(3) Stiff stems which do not require staking;
(4) Many very wide bracts which give the plant a full and complete appearance;
(5) Retention of the bracts, foliage and influorescences for an unusually long period of time after reaching maturity;
(6) A habit of not requiring light to delay bud set;
(7) A habit of setting buds quite easily under higher night temperatures and longer day lengths than other poinsettia varieties;
(8) A good pinching habit which produces 3 or more breaks;
(9) A normally later blooming habit than other varieties, but having the ability to be satisfactorily brought into bloom and to full maturity in every month of the year through the exercise of proper greenhouse cultural techniques;
(10) A distinctive, attractive, slightly ruffled appearance of the bracts and their absence of any tendency to droop with age;
(11) A distinctive and attractive pink color of the bracts corresponding to near Delft Rose which remains very stable;
(12) Absence of drooping and good retention of the inflorescence position relative to the bracts without rising as occurs in other varities as the inflorescences approach maturity; and

(13) Excellent keeping qualities, with consequent suitability for home decoration.

The accompanying drawing shows a typical specimen plant of my new variety as depicted in color as nearly true as it is reasonably possible to make the same in a color illustration of this character.

Although the details of my new sport, except for the bract color, are substantially identical with those described in Plant Patent No. 2,923, to which reference may be readily had, the following description is given for convenience, with color terminology in accordance with Wilson's Horticultural Colour Chart, except where general color terms of ordinary dictionary significance are obvious:

Locality where grown and observed: Encinitas, Calif.
Propagation: Holds its distinguishing characteristics through succeeding propagations by vegetative cuttings.
Parentage: Sport of poinsettia variety known as #C–1.
Form: Medium tall; upright; graceful contour.
Habit of growth: Vigorous grower but not too tall.
Rooting habit: Very fast (from 12 to 15 days under mist); vigorous; extensive; uniform.
Blooming habit: Approximately 10 to 11 weeks after start of short days.
Blooming season: Naturally in December, but has excellent suitability for forcing in every month of the year by appropriate greenhouse culture practices.
Foliage: Alternate; borne horizontally on stems; persistent; normal abundance.
*Size.*—Medium; borne on short petioles; from about 3 inches to 6 inches long; from about 2½ inches to 5 inches wide.
*Shape.*—Little serration; wide at base and abruptly tapering to long point at tip.
*Texture.*—Upper side—medium glossy; medium smooth; with ordinary recessed veins. Underside—dull; with ordinary protruding veins.
*Margin.*—Well defined.
*Color.*—New foliage—Upper side—Near Scheele's Green, Plate 860, page 175. Lower side—Near Scheele's Green, Plate 860/1, page 175. Old foliage—Upper side—Near Ivy Green, Plate 0001060, page 200. Lower side—Near Leek Green, Plate 000858, page 197.
Disease Resistance: Resistant to rhizoctonia and pythium stem and root rot during propagation and growing period, and very resistant to botrytis during blooming period, as determined by comparison with other plants grown under the same cultural conditions at Encinitas, Calif., which are infected with these diseases.
Bracts: Many (approximately 15 to 20 in number); very wide; excellent retention; new bracts form and develop as other bracts mature; very long lasting qualities; short pointed when young, but becoming long pointed at maturity; retain relative position and do not droop when mature or as bracts continue to age; retain their color exceptionally well; slightly ruffled in appearance; have short petioles giving a full appearance; tight center giving inflorescence form which creates an attractive appearance. Color—Near Delft Rose, Plate 020/2.
Flowers:
*Borne.*—Continuously for several months; many flowers per stem in regular clusters in varying stages of development; borne on strong, very short stems; slow development, giving a compact appearance for a greater period of time; position of the flowers remain relatively low without rising as it does in other commercial poinsettia varieties during early development, and does not spread out during later stages of development, thereby giving a more attractive appearance for a longer period of time.

*Quantity of bloom.*—Relatively abundant; continuous; flowers gradually drop off after maturity; flower clusters remain tight but new ones do not continue to develop; centers do not spread.

*Buds.*—From medium to large size; borne on Light Green stems. Color—Near Lettuce Green, Plate 861/3, page 176.

Reproductive organs:

*Stamens.*—Few; from ⅛ inch to ½ inch long. Color—Near Claret Rose, Plate 021, page 109.

*Pollen.*—Color—Near Naples Yellow, Plate 403, page 121.

*Styles.*—Color—Near Rose Opal, Plate 022, page 110.

*Ovaries.*—Color—Near Lettuce Green, Plate 022, page 110.

*Nectar cups.*—Near Egyptian Buff, Plate 407, page 122.

I claim:

1. A new and distinct variety of poinsettia plant, substantially as herein shown and described, characterized particularly as to novelty by a unique combination of characteristics which are substantially identical in all respects to those of the poinsettia variety known as #C–1 (Plant Patent No. 2,923) except for its bract color, said bracts being a distinctive and attractive pink color corresponding to near Delft Rose, as distinguished from the normal red color of the bracts of the variety #C–1.

No references cited.

ROBERT E. BAGWILL, Primary Examiner